US010084971B2

(12) United States Patent
Liu et al.

(10) Patent No.: US 10,084,971 B2
(45) Date of Patent: Sep. 25, 2018

(54) METHOD FOR MEASUREMENT AND 3D RECONSTRUCTION OF PRECIPITATION PARTICLES BASED ON ORTHOGONAL DUAL-VIEW IMAGING

(71) Applicant: National University of Defense Technology, Changsha (CN)

(72) Inventors: Xichuan Liu, Changsha (CN); Taichang Gao, Changsha (CN); Lei Liu, Changsha (CN); Shijun Zhao, Changsha (CN); Dongli Zhai, Changsha (CN)

(73) Assignee: NATIONAL UNIVERSITY OF DEFENSE TECHNOLOGY, Changsha (CN)

( * ) Notice: Subject to any disclaimer, the term of this patent is extended or adjusted under 35 U.S.C. 154(b) by 0 days.

(21) Appl. No.: 15/800,565

(22) Filed: Nov. 1, 2017

(65) Prior Publication Data
US 2018/0124328 A1 May 3, 2018

(30) Foreign Application Priority Data
Nov. 2, 2016 (CN) .......................... 2016 1 0951078

(51) Int. Cl.
| | |
|---|---|
| H04N 5/265 | (2006.01) |
| G01N 15/02 | (2006.01) |
| G06K 9/40 | (2006.01) |
| G06K 9/62 | (2006.01) |
| H04N 5/04 | (2006.01) |
| H04N 5/225 | (2006.01) |
| H04N 5/247 | (2006.01) |
| H04N 5/335 | (2011.01) |

(Continued)

(52) U.S. Cl.
CPC ......... *H04N 5/265* (2013.01); *G01N 15/0227* (2013.01); *G01N 15/147* (2013.01); *G01N 15/1475* (2013.01); *G06K 9/40* (2013.01); *G06K 9/6202* (2013.01); *H04N 5/04* (2013.01); *H04N 5/2256* (2013.01); *H04N 5/247* (2013.01); *H04N 5/335* (2013.01); *G01N 2015/0046* (2013.01)

(58) Field of Classification Search
CPC ..................................................... H04N 5/265
USPC ....................................................... 348/262
See application file for complete search history.

(56) References Cited

U.S. PATENT DOCUMENTS

| | | | | |
|---|---|---|---|---|
| 2013/0010098 | A1* | 1/2013 | Kalkbrenner | G01N 21/6428 348/79 |
| 2014/0320708 | A1* | 10/2014 | Marks | G02B 13/06 348/262 |

* cited by examiner

Primary Examiner — Joel Fosselman
(74) Attorney, Agent, or Firm — Treasure IP Group, LLC

(57) ABSTRACT

This invention discloses a method for measurement and 3D reconstruction of precipitation particles based on orthogonal dual-view imaging. An orthogonal 3D sampling space are formed by a pair of line camera and continuum light source, two pairs of planar cameras and pulse light sources placed orthogonally. The line camera scans with a speed no less than 20,000 lines per second, two cameras and pulse light sources are triggered when the line camera detects the particles in sampling area, two orthogonal images are recorded by two planar cameras using the double-exposure or multiple-exposure in one frame. The 3D images of particles are obtained by pixel matching and grid reconstruction method, based on which the 3D sizes, axis ratio, orientation, fall velocity, and other characteristics of particles are calculated. This method can measure the 3D micro-physical characteristics of precipitation particles automatically and precisely.

6 Claims, 2 Drawing Sheets

(51) Int. Cl.
*G01N 15/14* (2006.01)
*G01N 15/00* (2006.01)

METHOD FOR MEASUREMENT AND 3D RECONSTRUCTION OF PRECIPITATION PARTICLES BASED ON ORTHOGONAL DUAL-VIEW IMAGING

CROSS REFERENCE TO RELATED APPLICATION

This application claims priority to a Chinese Application No. 201610951078.0 filed on Nov. 2, 2016. The Chinese Application is incorporated herein by reference in its entirety.

FIELD OF THE INVENTION

The present invention discloses a method for Measurement and 3D reconstruction of Precipitation particles based on orthogonal dual-view imaging, which measures the three-dimensional shape of the precipitation particles. The present invention relates to the field of automated weather systems.

DESCRIPTION OF PRIOR ART

Precipitation is defined as the condensation of atmospheric water vapor that falls under gravity, including drizzle, rain, sleet, snow, graupel, hail, and etc. The precipitation particles take on different size, shape, fall velocity, and spatial distribution in the falling procedure, in which the three-dimensional shape, axis ratio, and orientation play key roles in many fields, such as precipitation physics, electromagnetic wave attenuation induced by rain, remote sensing of radar, and etc. However, existing instruments can only measure the raindrop size distribution, the three-dimensional shape of precipitation particles cannot be measured obtained and analyzed.

At present, the rain gauge, tipping bucket rain gauge, weighing rain gauge, and optical rain gauge can only measure the rainfall accumulation and rainrate; the Joss-Waldvogel disdrometer (short for JWD) can measure the size distribution of raindrops based on the impact of raindrops on the sampling area; OTT PARSIVEL disdrometer (short for OTT) can measure the horizontal size and fall velocity of raindrops based on the empirical shape model of raindrops, both the JWD and OTT cannot measure the shape of raindrops. The 2D Video Disdrometer (short for 2DVD) can measure the shape and fall velocity of raindrops by two orthogonal line-scan cameras, but the horizontal motion of the droplet in the presence of horizontal winds are prone to cause a distorted image of the raindrops, the errors in the drop shape measurement still exist after a distortion correction. Snow Video Imager (SVI) can only measure the two-dimensional shapes of snowflakes using a planar CCD camera.

Accordingly, the 3D characteristics measurements of precipitation particles still are obviously inadequate, which cannot fulfill the imperative need of related field.

SUMMARY OF THE INVENTION

The object of the present invention is to provide a method for measurement and 3D reconstruction of precipitation particles based on the orthogonal dual-view imaging, 3D characteristics of precipitation particles can be obtained in real-time using the binocular vision imaging method.

The system preferably includes two planar CCD/CMOS cameras, two pulse light sources, a high-speed line image sensor, and a continuous light source. The detailed steps are as follows.

a. Two pulse light sources generate two parallel light beams that are projected onto two planar cameras separately. A series of telecentric lens are used to extend the depth of field of imaging systems. Two parallel light beams are orthogonal to each other, the overlap of two light beams forms the 3D sampling space.

b. The continuous light source generates a parallel light sheet that is projected onto the line image sensor, the light sheet is placed exactly above the 3D sampling space.

c. The pulse light sources and planar cameras are timing synchronous precisely by the MPU, which ensure the exposure of planar camera illuminated by the pulse light source.

d. The line image sensor scans the sampling area with a high-speed in real-time, when the precipitation particles passing through and are detected, an instruction sequence is generated and transmitted to the MPU, triggering the image acquisition of two planar cameras.

e. The pulse light sources illuminate the 3D sampling space in a certain frequency, and two planar cameras record two orthogonal 2D images of precipitation particles in different time-sequences separately.

f. 3D image of each precipitation particle is reconstructed from two 2D images by using but not limited to the pixel matching method.

g. The 3D sizes, axis ratio, orientation, fall velocity, and other characteristics are calculated based on the 3D images of precipitation particles.

The electronic shutters of two planar cameras are synchronized with the pulse light sources in sequence coordination, by which the particles falling through the 3D sampling space can be recorded by two planar cameras at the same time. The telecentric lens are used to ensure the clear imaging.

The line image sensor scans with a speed no less than 20,000 lines per second, by which the precipitation particle falling through the sampling area can be detected.

The pulse light sources are triggered when the line image sensor detects the particle in sampling area, the exposure sequence includes but not limited to the double-exposure or multiple-exposure in one frame.

The Micro Process Unit (MPU) connects and controls the work of two planar cameras, two pulse light sources, and a line image sensor.

The valid sampling space are formed by a beam and two orthogonal cylinders. The overlap of two orthogonal cylinders forms the 3D sampling space.

The present invention describes a method for measurement and 3D reconstruction of precipitation particles based on orthogonal dual-view imaging, compared with the existing methods, the line image sensor can monitor the particles with a high speed. Further, the 3D images of particles can be measured and reconstructed by two orthogonal cameras, by which the 3D sizes, axis ratio, orientation, and other characteristics can be obtained. It can address the disadvantages of linear or planar measurement in a single view, the planar and line image sensors are low in cost, therefore this method is convenient for application.

DESCRIPTION OF THE DRAWINGS

Various objects, features, and advantages of the present invention can be fully appreciated with reference to the following detailed description of the invention when considered in connection with the following drawings, in which like reference numerals identify like elements.

DETAILED DESCRIPTION OF THE EMBODIMENTS OF THE INVENTION

Figure 1:
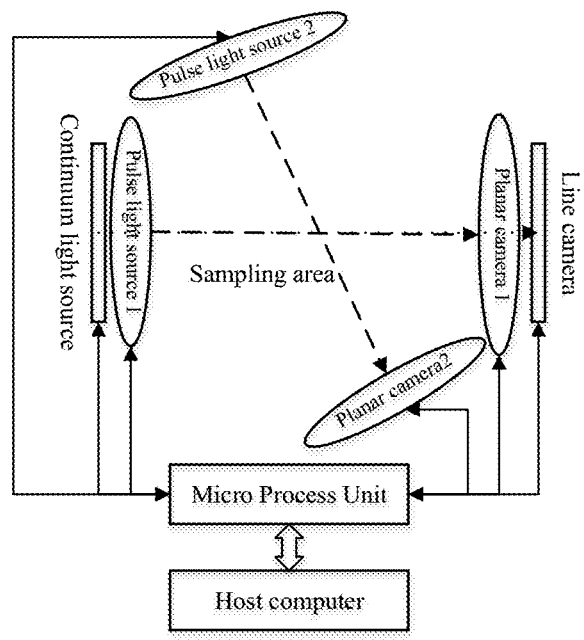
FIG. 1 is the structure diagram of this invention.
Figure 2:
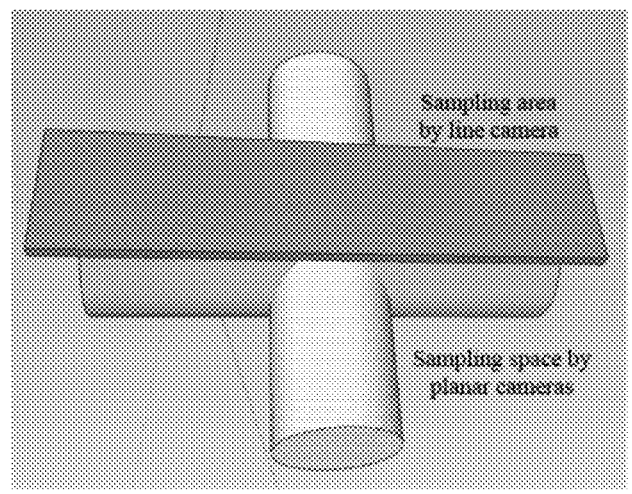
FIG. 2 is the optical path diagram of this invention.
Figure 3:
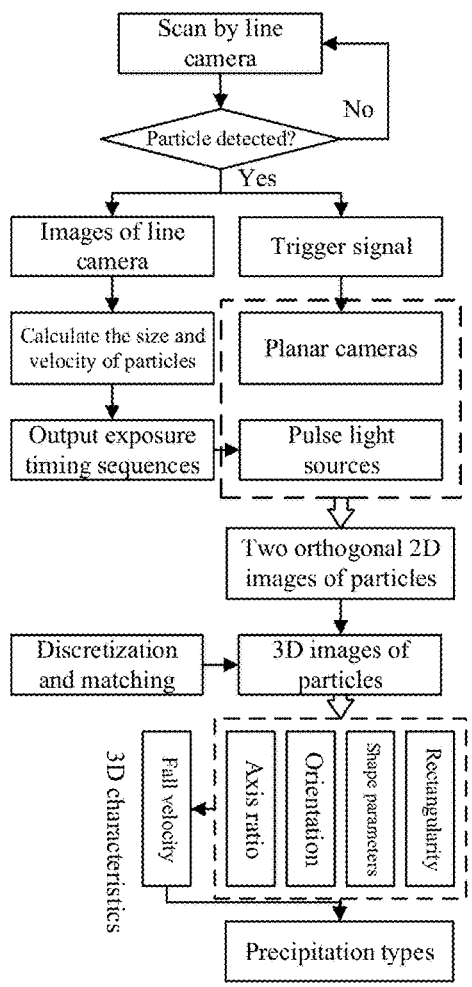
FIG. 3 is a work flowchart of this invention.
Figure 4:
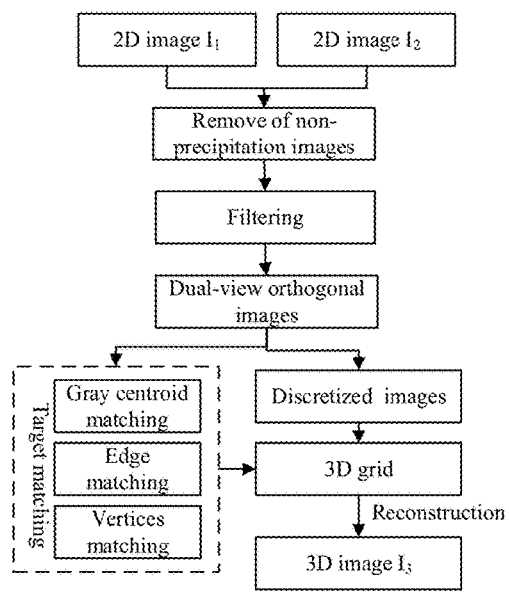
FIG. 4 is a flowchart of 3D reconstruction of raindrops.

The present invention described herein is directed to a method for measurement and 3D reconstruction of precipitation particles based on orthogonal dual-view imaging. The 3D precipitation measurement system preferably includes two planar cameras, two pulse light sources, a high-speed line image sensor, a continuous light source, and a micro process unit (MPU). Two planar cameras are placed facing towards two pulse light sources separately, two parallel light beams are orthogonal to each other, the overlap of two light beams forms the 3D sampling space. The MPU connects and controls the work of two planar cameras, two pulse light sources, and a line image sensor, the raw data of two planar cameras and a line image sensor are collected and transmitted to the host computer. Software in the host computer reconstructs the 3D images of precipitation particles, based on which the 3D sizes, axis ratio, orientation, fall velocity, and other characteristics can be obtained.

The continuous light source generates a parallel light sheet that is projected onto the line image sensor, the light sheet is placed exactly above the 3D sampling space. The line image sensor scans the sampling area with a high-speed in real-time, when the precipitation particles passing through and are detected, an instruction sequence is generated and transmitted to the MPU, triggering the image acquisition of two planar cameras.

Two planar cameras are synchronized with two pulse light sources separately, the exposure sequence includes but not limited to the double-exposure or multiple-exposure in one frame, by which the 3D images and movement of particles in sampling space can be measured.

Both the planar and line imaging use the telecentric lens to extend the depth of field of imaging systems. The light sources use but not limited to the multi-mode cluster fiber, and outgoing beams from the expander lens form the parallel light beams.

3D image of each precipitation particle is reconstructed from two 2D images by using but not limited to the pixel matching method. The 3D sizes, shape parameters, rectangularity, corner number, axis ratio, fall velocity of particles can be calculated, based on which the raindrops, snowflakes, and graupels can be identified according to a certain threshold values of above parameters.

In one embodiment of the present invention, the 3D characteristics of precipitation particles are obtained using the following steps:

1. High-speed scan of line image sensor in real-time. Illuminated by the continuos light source, the line CCD or CMOS camera records the images of particles and triggers the double planar imaging. The detail process includes:

a. The line image sensor scans with a speed no less than 20,000 lines per second, by which the discrete section images of particles falling through the sampling area can be recorded.

b. Discrete section widths of individual particle in time sequences are obtained by a binarization threshold value. The vertical size of each particle is estimated by its maximum horizontal size and the empirical axis ratio relationship, based on which the 2D images of particles are obtained according to the empirical relationship of fall velocity and diameter.

c. There is no trigger signal when line image sensor detects no particle, and when the line image sensor detects particles fall through the sampling area, MPU generates and transmits the trigger signal to the planar cameras and pulse light sources.

2. Acquisition of dual-field images by two planar cameras. When the trigger signal is detected, the pulse light sources are activated, and two cameras record two orthogonal images by using double-exposure or multiple-exposure in one frame synchronously in real-time.

3. 3D reconstruction of precipitation particles.

a. Image pre-processing. The images of water marks, insects, or other non-precipitation factors are removed by using but not limited to the pixel grey scale, shape parameter, and image edge detection method. The effective images are obtained after noise reduction and filtering.

b. According to the position of particles sampled in the 3D sampling space, two images of one particles in two orthogonal angles are paired by using but not limited to the gray centroid matching, edge matching, and vertices matching method.

c. A three-dimensional grid is divided with 1-pixel resolution, two orthogonal two-dimensional images are discretized and corresponded to the three-dimensional grid.

d. The particles in three-dimensional grid are represented by gray-scale value. For example, the gray value of 0 denotes no image observed, the gray value of 1~255 denotes the images obscured by particles, the gray value increases with the decrease of light intensity of the particle occlusion. Thus, the 3D images of precipitation particles can be reconstructed based on the 3D pixel distribution in space.

4. Extraction of 3D characteristics of particles. The 3D sizes, gray intensity, and density of particles are obtained from the 3D images of particles, based on which the 3D axis ratio, orientation, shape parameters, rectangularity, corner number, and other features are calculated, the fall velocity of particles are calculated from the double-exposure or multiple-exposure in one frame images based on the feature matching and time matching. The raindrops, snowflakes, graupels and other precipitation types can be identified based on the above parameters.

We claim:

1. A method for performing measurement and 3D reconstruction of precipitation particles based on orthogonal dual-view imaging, using a system comprised of two planar CCD/CMOS cameras, two pulse light sources, a high-speed line image sensor, and a continuous light source, which are connected with telecentric lens, a microprocessor unit (MPU), and a host computer, wherein the two planar cameras are placed facing towards the two pulse light sources respectively, two parallel light beams from the two pulse light sources are orthogonal to each other, an overlap region of the two light beams forms a 3D sampling space;

the continuous light source, across from the line image sensor, generates a parallel light sheet that is projected onto the line image sensor, wherein the continuous light source, the line image sensor and the telecentric lens forms a wide sampling space, the light sheet is placed directly above the 3D sampling space;

the two planar cameras, two pulse light sources and a line image sensor are connected to the MPU and timing sequences of the two planar cameras and two pulse light sources are synchronized precisely by the MPU, when particles pass through are detected by the line image sensor, the MPU generates and transmits an instruction sequence to trigger the image acquisition by the two planar cameras;

the method comprising controlling the two planar cameras, by timing sequences synchronized by the MPU, and recording two 2D images of each particle at two orthogonal angles at the same time;

reconstructuring a 3D image of each precipitation particle from the two orthogonal 2D images by using a pixel matching method; and calculating characteristics of the precipitation particles, including 3D sizes, axis ratio, orientation, fall velocity, and other characteristics based on the 3D images of the precipitation particles.

2. The method according to claim 1, wherein the line image sensor can scan the 3D sampling space with a high-speed in real-time, an instruction sequence signal is generated and transmitted to trigger the planar cameras when the line image sensor detects the particles, otherwise there is no trigger signal output.

3. The method according to claim 1, wherein the two planar cameras and two pulse light sources are synchronized in exposure timing sequences precisely, two orthogonal images of each particles are obtained by using double-exposure or multiple-exposure in one frame.

4. The method according to claim 2, wherein the exposure time and time interval between several exposures depend on the result of high-speed line image sensor, short exposure time and time interval are adopted when large particles with great velocity are detected, whereas long exposure time and time interval are adopted when small particles with little velocity are detected, the exposure time and time interval can be adjusted automatically.

5. The method according to claim 1, wherein the 3D reconstruction of precipitation particles further comprises a. pre-processing images to remove images of water marks, insects, or other non-precipitation factors by using one or in combination of pixel grey scale, shape parameter, and image edge detection method; and obtaining effective images after noise reduction and filtering;

b. pairing the two images of one particles in two orthogonal angles, According to the position of particles sampled in the 3D sampling space, by using one or in combination of gray centroid matching, edge matching, and vertices matching method;

c. dividing a three-dimensional grid with 1-pixel resolution, and two orthogonal two-dimensional images are discretized and identified to the three-dimensional grid;

d. representing particles in the three-dimensional grid by gray-scale value including setting up grey value at 0 as no precipitation particle, a grey value of 1~255 as the images obscured by particles, because the gray value increases as more particles to obstruct the light causing a reduced transmission, and obtaining a 3D pixel distribution of the participation particles in space and reconstructing the 3D images of precipitation particles based on the 3D pixel distribution in space.

6. The method according to claim 1, wherein the 3D sizes, gray intensity, and density of particles are obtained from the 3D images of the precipitation particles, are used to calculate the 3D axis ratio, orientation, shape parameters, rectangularity, corner number, and other features the fall velocity of particles are calculated from the double-exposure or multiple-exposure in one frame images based on the feature matching and time matching, so that precipitation types including raindrops, snowflakes, granules and other precipitation types can be identified based on the above parameters.

* * * * *